United States Patent [19]

Ashwood et al.

[11] Patent Number: 4,616,021
[45] Date of Patent: Oct. 7, 1986

[54] CHROMAN DERIVATIVES

[75] Inventors: Valerie A. Ashwood, Bishop's Stortford; John M. Evans, Roydon, both of England

[73] Assignee: Beecham Group p.l.c., England

[21] Appl. No.: 722,709

[22] Filed: Apr. 12, 1985

[30] Foreign Application Priority Data

Apr. 14, 1984 [GB] United Kingdom ............... 8409745

[51] Int. Cl.⁴ .................... A61K 31/47; A61K 31/40; C07D 405/04
[52] U.S. Cl. .................... 514/309; 514/414; 546/141; 548/454
[58] Field of Search ............. 546/141, 196; 548/454; 314/309; 514/414

[56] References Cited

U.S. PATENT DOCUMENTS 4,446,113  5/1984  Evans et al. ............... 546/196
4,510,152  4/1985  Faruk ..................... 546/196

Primary Examiner—Robert T. Bond
Attorney, Agent, or Firm—Jacobs & Jacobs

[57] ABSTRACT

A compound of formula (I):

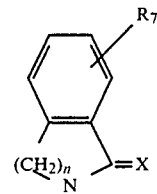
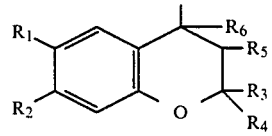

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or —C($C_{1-6}$ alkyl)NOH or —C($C_{1-6}$ alkyl)NNH₂, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is hydrogen, $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl;
X is oxygen or sulphur;
n is 1 or 2; the nitrogen-containing group in the 4-position being trans to the $R_5$ group when $R_5$ is hydroxy, $C_{1-6}$ alkoxy or $C_{1-7}$ acyloxy; or a pharmaceutically acceptable salt or solvate thereof. The compounds of the invention are useful for lowering blood pressure.

9 Claims, No Drawings

CHROMAN DERIVATIVES

The present invention relates to novel chromans and chromenes having pharmacological activity, to a process for preparing them, to pharmaceutical compositions containing them, and to their use in the treatment of animals.

U.S. Pat. Nos. 4,110,347, 4,119,643 and 4,251,537 and European Patent Pulbication Nos. 28 064 and 28 449 disclose classes of compounds that are described as having blood pressure lowering activity or anti-hypertensive activity.

European Patent Publication Nos. 76 075, 91 748, 93 534 and 95 310 disclose classes of chromans that are described as having blood pressure lowering activity. In addition, European Patent Publication No. 93 535 discloses a class of chromans and chromenes that are also described as having blood pressure lowering activity.

A further class of chromans and chromenes has now been discovered whjich have a tetrahydroisoquinolin-1-on-2-yl, tetrahydroisoquinolin-1-thion-2-yl, 1-oxo-1,3-dihydroisoindol-2-yl or 1-thioxo-1,3-dihydroisoindol-2-yl moiety that substitutes th chroman or chromene in the 4-position. In addition, such chromans and chromenes have been found to have blood pressure lowering activity.

Accordingly, the present invention provides a compound of formula (I):

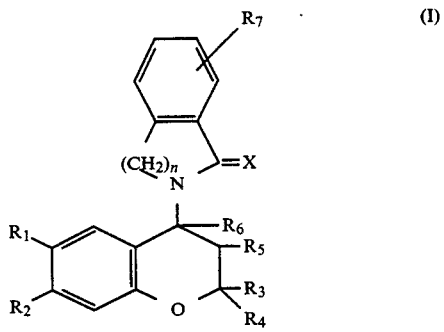

wherein:
either one of $R_1$ and $R_2$ is hydrogen and the other is selected from the class of $C_{1-6}$ alkylcarbonyl, $C_{-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or -C($C_{1-6}$ alkyl)-NOH or -C($C_{1-6}$ alkyl)NNH$_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl;
one of $R_3$ and $R_4$ is hydrogen or $C_{1-4}$ alkyl and the other is $C_{1-4}$ alkyl or $R_3$ and $R_4$ together are $C_{2-5}$ polymethylene;
either $R_5$ is hydrogen, hydroxy, $C_{1-6}$ alkoxy or $C_{1-7}$ acyloxy and $R_6$ is hydrogen or $R_5$ and $R_6$ together are a bond;
$R_7$ is hydrogen, $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl;
X is oxygen or sulphur;
n is 1 or 2; the nitrogen-containing group in the 4-position being trans to the $R_5$ group when $R_5$ is hydroxy, $C_{1-6}$ alkoxy or $C_{1-7}$ acyloxy; or a pharmaceutically acceptable salt or solvate thereof.

When one or $R_1$ and $R_2$ is hydrogen, the other is preferably selected from the class of $C_{1-6}$ alkylcarbonyl, $C_{1-6}$ alkoxycarbonyl, nitro and cyano. In particular, when one of $R_1$ and $R_2$ is hydrogen, the other is preferably acetyl, nitro or cyano, especially nitro or cyano.

When one or $R_1$ and $R_2$ is hydrogen, it is preferred that $R_2$ is hydrogen.

When one of $R_1$ and $R_2$ is nitro, cyano or $C_{1-3}$ alkylcarbonyl, the other is preferably amino optionally substituted by one or two $C_{1-6}$ alkyl or by $C_{2-7}$ alkanoyl. In particular, when one of $R_1$ and $R_2$ is nitro, cyano or $C_{1-3}$ alkylcarbonyl, the other is amino, methylamino, dimethylamino or acetylamino. Most preferably, one of $R_1$ and $R_2$ is nitro or cyano, especially cyano and the other is amino.

When one of $R_1$ and $R_2$ is nitro, cyano or $C_{1-3}$ alkylcarbonyl, it is preferred that $R_1$ is nitro, cyano or $C_{1-3}$ alkylcarbonyl.

The alkyl groups or alkyl moieties of alkyl-containing group for $R_1$ and $R_2$ are, preferably, methyl or ethyl.

Preferably, $R_3$ and $R_4$ are both $C_{1-4}$ alkyl. In particular, they are both methyl or ethyl, preferably both methyl.

When $R_5$ is $C_{1-6}$ alkoxy and $R_6$ is hydrogen, preferred examples of $R_5$ include methoxy and ethoxy, of which methoxy is more preferred. When $R_5$ is $C_{1-7}$ acyloxy and $R_6$ is hydrogen, a preferred class of $R_5$ is unsubstituted carboxylic acyloxy, such as unsubstituted aliphatic acyloxy or benzoyloxy. However, it is more preferred that $R_5$ and $R_6$ together are a bond or that $R_5$ and $R_6$ are both hydrogen, or, in particular, that $R_5$ is hydroxy and $R_6$ is hydrogen.

When $R_7$ is $C_{1-12}$ carboxylic acyl, preferred examples thereof include $C_{1-6}$ alkylcarbonyl, $C_{1-6}$ alkoxycarbonyl and carboxy.

When $R_7$ is $C_{1-6}$ alkyl or is a $C_{1-6}$ alkyl-containing group, the alkyl moiety is, preferably, methyl or ethyl.

Preferably, $R_7$ is hydrogen.

Preferably, X is oxygen.

Examples of a pharmaceutically acceptable salt of a compound formula (I) include the acid addition salts of a compound of formula (I), wherein one or the other of $R_1$ or $R_2$ is an amino or an amino-containing group, or wherein $R_7$ is amino, for example the hydrochloride and hydrobromide salts.

Examples of a pharmaceutically acceptable solvate of a compound of formula (I) include the hydrate.

Preferably, a compound of formula (I) is in substantially pure form.

The compounds of formula (I), wherein $R_5$ is hydrogen, hydroxy, $C_{1-6}$ alkoxy or $C_{1-7}$ acyloxy and $R_6$ is hydrogen, are asymmetric and, therefore, can exist in the form of optical isomers. The present invention extends to all such isomers individually and as mixtures, such as racemic modifications.

Examples of compounds of formula (I) include the compound prepared in the Example hereinafter.

The present invention also provides a process for the preparation of a compound of formula (I), which comprises the reaction of a compound of formula (II):

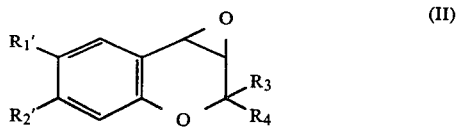

wherein $R_1^1$ is $R_1$ as defined hereinbefore or a group or atom convertible thereto, $R_2^1$ is $R_2$ as defined hereinbefore or a group or atom convertible thereto, and $R_3$ and $R_4$ are as defined hereinbefore, and a compound of formula (III):

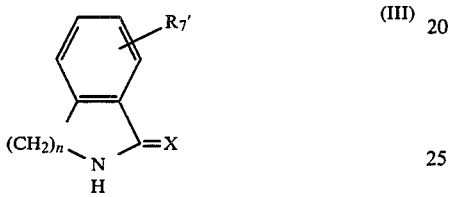

wherein $R_7^1$ is $R_7$ as defined hereinbefore or a group or atom convertible thereto, and X and n are as defined hereinbefore; in the case where $R_1^1$ is a group or atom convertible into $R_1$, converting the group or atom into $R_1$; in the case where $R_2^1$ is a group or atom convertible into $R_2$, converting the group or atom into $R_2$; in the case where $R_7^1$ is a group or atom convertible into $R_7$, converting the group or atom into $R_7$; optionally converting $R_1$ and/or $R_2$ and/or $R_7$ in the resulting compound of formula (I) into another $R_1$, $R_2$ or $R_7$ respectively; optionally converting the resulting compound of formula (I), wherein $R_5$ is hydroxy and $R_6$ is hydrogen, into another compound of formula (I), wherein $R_5$ is $C_{1-6}$ alkoxy or $C_{1-7}$ acyloxy and $R_6$ is hydrogen; optionally dehydrating the resulting compound of formula (I), wherein $R_5$ is hydroxy and $R_6$ is hydrogen, so as to obtain the corresponding compound of formula (I), wherein $R_5$ and $R_6$ together are a bond; optionally reducing the resulting compound of formula (I), wherein $R_5$ and $R_6$ together are a bond, so as to obtain the corresponding compound of formula (I), wherein $R_5$ and $R_6$ are both hydrogen; in the case where in the resulting compound of formula (I), X is oxygen, optionally thiating the compound so as to obtain the corresponding compound of formula (I), wherein X is sulphur; and optionally forming a pharmaceutically acceptable salt or solvate.

It is particularly preferred that the reaction between the compounds of formulae (II) and (III) is carried out under basic conditions so as to facilitate the formation of the anion of the compound of formula (III), for example, in the presence of sodium hydride.

Examples of conversions of a group or atom for $R_1^1$ or $R_2^1$ into $R_1$ or $R_2$ are generally known in the art of aromatic chemistry. For example, if it is desired to obtain a compound of formula (I), wherein one of $R_1$ and $R_2$ is hydrogen and the other is nitro, it is possible to carry out the reaction between the compounds of formulae (II) and (III) with one of $R_1^1$ and $R_2^1$ being hydrogen and the other being acetamido and then to nitrate the resulting compound in conventional manner and subsequently to convert the acetamido group into a hydrogen atom by hydrolysis, diazotisation and decomposition in conventional manner.

Examples of conversions of a group or atom for $R_7^1$ into $R_7$ are generally known in the art of aromatic chemistry as for $R_1^1$ and $R_2^1$ above.

If the optional conversion of the resulting compound of formula (I), wherein $R_5$ is hydroxy and $R_6$ is hydrogen, into another compound of formula (I), wherein $R_5$ is $C_{1-7}$ acyloxy and $R_6$ is hydrogen, is to be carried out, then it is preferred first to protect any unsubstituted terminal amine that may be present for $R_1$, $R_2$ or $R_7$ and after the acylation reaction to convert the protected amino moiety into the required terminal amine. Examples of protecting agents and their addition and removal are generally known in the art.

If, in the case where, in the resulting compound of formula (I), X is oxygen, the optional thiation of the compound is to be carried out so as to obtain the corresponding compound of formula (I), wherein X is sulphur, then it is preferred first to protect any carbonyl function that may be present as part of the group for $R_1$, $R_2$ or $R_7$ and, after the thiation, to convert the protected carbonyl-containing group into the required group for $R_1$, $R_2$ or $R_7$. Examples of preferred carbonyl protecting group include ketalising agents, which may be added and removed in conventional manner.

Examples of an optional conversion of $R_1$ or $R_2$ in the resulting compound of formula (I) into another $R_1$ or $R_2$, as defined hereinbefore, include the optional conversion of an α-hydroxyethyl group into acetyl by oxidation, the optional conversion of an amino group into a chloro atom by diazotisation and reaction with a chloride salt, the optional conversion of an amino group into an amino group substituted by one or two $C_{1-6}$ alkyl or by $C_{2-7}$ alkanoyl, or the optional conversion of a hydrogen atom into a nitro group by nitration.

The optional conversion of $R_7$ in the resulting compound of formula (I) into another $R_7$, as defined hereinbefore may be carried out by conventional procedures, such as by the appropriate examples given for the optional conversion of $R_1$ or $R_2$ above.

The optional conversion of $R_7$ the resulting compound of formula (I), wherein $R_5$ is hydroxy and $R_6$ is hydrogen, into another compound of formula (I), wherein $R_5$ is $C_{1-6}$ alkoxy or $C_{1-7}$ acyloxy and $R_6$ is hydrogen, may be carried out respectively by alkylation using an alkyl iodide in an inert solvent, such as toluene, in the presence of a base, such as potassium hydroxide, or by acylation using a carboxylic acid chloride or anhydride in a non-hydroxylic solvent in the presence of a base such as trimethylamine, triethylamine or piperidine.

The optional dehydration of the resulting compound of formula (I), wherein $R_5$ is hydroxy and $R_6$ is hydrogen, so as to obtain the corresponding compound of formula (I), wherein $R_5$ and $R_6$ together are a bond, may be carried out under conventional dehydration conditions, for example, by using a dehydrating agent, such as sodium hydride, in an inert solvent, such as dry tetrahydrofuran, at reflux temperature.

The optional reduction of the resulting compound of formula (I), wherein $R_5$ and $R_6$ together are a bond, so as to obtain the corresponding compound of formula (I), wherein $R_5$ and $R_6$ are both hydrogen, may be carried out in conventional manner by catalytic hydrogenation using palladium on charcoal.

In the case where, in the resulting compound of formula (I), X is oxygen, the optional thiation of the compound may be carried out so as to obtain the corresponding compound of formula (I), wherein X is sulphur, with conventional thiation agents, such as hydrogen sulphide, phosporous pentasulphide and Lawesson's reagent (p-methoxyphenylthiophosphine sulphide dimer). The use of hydrogen sulphide and phosporous pentasulphide may lead to side-reactions and, therefore, the use of Lawesson's reagent is preferred.

The thiation reaction conditions are conventional for the thiation agent employed. For example, the use of hydrogen sulphide is, preferably, acid catalysed by, for example, hydrogen chloride in a polar solvent, such as acetic acid or ethanol. The preferred use of Lawesson's reagent is preferably carried out under reflux in a dry solvent, such as toluene or methylene chloride.

The optional formation of a pharmaceutically acceptable salt, when any of $R_1$, $R_2$ and $R_7$ in the resulting compound of formula (I) is amino or anamino-containing group, may be carried out conventionally.

The compounds of formula (II) are known compounds and can be prepared in accordance with the processes described in the aforementioned U.S. patents and European Patent Publications, the contents of which are incorporated herein by reference.

The compounds of formula (III) are also known compounds or can be prepared by conventional procedures from known compounds.

As mentioned previously, the compounds of formula (I) have been found to have blood-pressure lowering activity. They are therefore useful in the treatment of hypertension.

The present invention accordingly provides a pharmaceutical composition which comprises a compound of this invention and a pharmaceutically acceptable carrier. In particular, the present invention provides an anti-hypertensive pharmaceutical composition which comprises an anti-hypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit-dose. Suitable unit dose forms include tablets, capsules and powders in sachets or vials. Such unit dose forms may contain from 1 to 100 mg of a compound of the invention and more usually from 2 to 50 mg, for example 5 to 25 mg such as 6, 10, 15 or 20 mg. Such compositions may be administered from 1 to 6 times a day, more usually from 2 to 4 times a day, in a manner such that the daily dose is from 1 to 200 mg for a 70 kg human adult and more particularly from 1 to 10 mg.

No toxicological effects are indicated for the compounds of the invention at the above dosage range.

The compositions of the invention may be formulated with conventional excipients, such as a filler, a disintegrating agent, a binder, a lubricant, a flavouring agent and the like. They are formulated in conventional manner, for example in a manner similar to that used for known anti-hypertensive agents, diuretics and β-blocking agents.

The present invention further provides a compound of the invention for use as an active therapeutic substance. Compounds of formula (I) are of particular use in the treatment of hypertension.

The present invention yet further provides a method of treating hypertension in mammals including man, which comprises adminstering to the suffering mammal an anti-hypertensive effective amount of a compound or a pharmaceutical composition of the invention.

The following example relates to the preparation of a compound of formula (I).

EXAMPLE 1

6-Cyano-3,4-dihydro-2,2-dimethyl-trans-4-(N-tetrahydro- isoquinolin-1-one)-2H-benzo[b]-pyran-3-ol (E1)

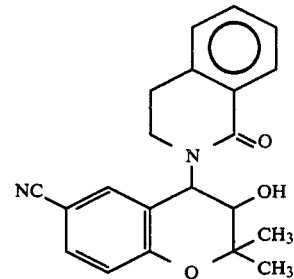

(E1)

To a mixture of 6-cyano-3,4-dihydro-2,2-dimethyl-3,4-epoxy-2H-benzo[b]pyran (1.27 g) and 1,2,3,4-tetrahydroisoquinolin-1-one (0.93 g) stirred in dry dimethyl sulphoxide (30 ml) was added sodium hydride (0.19 g, 80% dispersion in oil). After stirring at room temperature for 4 hours, water (60 ml) was added and the reaction stirred for 1 hour. The solid precipitate was filtered off, chromatographed and recrystallised from ethyl acetate-pentane, to give the title compound (0.45 g) as crystals of m.p. 218°–219° C.

NMR (CDCl$_3$)δ
1.35 (3H, s)
1.57 (3H, s)
2.80–3.05 (2H, m)
3.10–3.40 (3H, m) including 1H exchangeable with D$_2$O
3.65–3.93 (1H, m) collapsing to d, J=10 Hz on addition of D$_2$O
6.04 (1H, d, J=10 Hz)
6.92 (1H, d, J=10 Hz)
7.10–7.55 (5H, m)
7.98–8.15 (1H, m)

Pharmacological Data

Systolic blood pressures were recorded by a modification of the tail cuff method described by I. M. Claxton, M G Palfreyman, R. H. Poyser, R. L. Whiting, European Journal of Pharmacology, 37, 179 (1976).

A W+W BP recorder, model 8005, was used to display pulses prior to all measurements rats were placed in a heated environment (33.5°±0.5° C.) before transfer to a restraining cage. Each determination of blood pressure was the mean of at least 6 readings. Spontaneously hypertensive rates (ages 12–18 weeks) with systolic blood pressures >170 mmHg were considered hypertensive.

| Compound of Example 1 | Time Post Dose Hours | % Change in Systolic Blood Blood | % Change in Heart Rate |
|---|---|---|---|
| 6 rats | 1* | −56 ± 5 | −1 ± 2 |

| Compound of Example 1 | Time Post Dose Hours | % Change in Systolic Blood Blood | % Change in Heart Rate |
|---|---|---|---|
| Dose 10 mg/kg p.o. | 2** | −57 | −7 |
| Initial Blood Pressure 235 ± 4 mm Hg | 4*** | −41 | −1 |
| Initial Heart Rate 521 ± 8 beats/min | 6*** | −36 | −4 |

*2 rats had no measurable pulse
**4 rats had no measurable pulse
***3 rats had no measurable pulse

I claim:

1. A compound of formula (I):

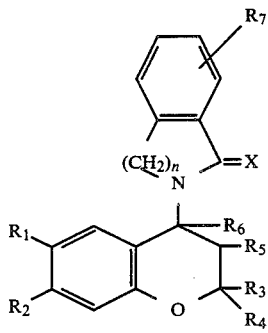

wherein:
either one of $R_1$ and $R_2$ is hydrogen and the other is selected from the class of $C_{1-6}$ alkylcarbonyl, $C_{1-6}$ alkoxycarbonyl, $C_{1-6}$ alkylcarbonyloxy, $C_{1-6}$ alkylhydroxymethyl, nitro, cyano, chloro, trifluoromethyl, $C_{1-6}$ alkylsulphinyl, $C_{1-6}$ alkylsulphonyl, $C_{1-6}$ alkoxysulphinyl, $C_{1-6}$ alkoxysulphonyl, $C_{1-6}$ alkylcarbonylamino, $C_{1-6}$ alkoxycarbonylamino, $C_{1-6}$ alkyl-thiocarbonyl, $C_{1-6}$ alkoxy-thiocarbonyl, $C_{1-6}$ alkyl-thiocarbonyloxy, 1-mercapto $C_{2-7}$ alkyl, formyl, or aminosulphinyl, aminosulphonyl or aminocarbonyl, the amino moiety being optionally substituted by one or two $C_{1-6}$ alkyl groups, or $C_{1-6}$ alkylsulphinylamino, $C_{1-6}$ alkylsulphonylamino, $C_{1-6}$ alkoxysulphinylamino or $C_{1-6}$ alkoxysulphonylamino, or ethylenyl terminally substituted by $C_{1-6}$ alkylcarbonyl, nitro or cyano, or -C($C_{1-6}$ alkyl)-NOH or -C($C_{1-6}$ alkyl)$NNH_2$, or one of $R_1$ and $R_2$ is nitro, cyano or $C_{1-3}$ alkylcarbonyl and the other is methoxy or amino optionally substituted by one or two $C_{1-6}$ alkyl or by $C_{2-7}$ alkanoyl; one of $R_3$ and $R_4$ is hydrogen or $C_{1-4}$ alkyl and the other is $C_{1-4}$ alkyl or $R_3$ and $R_4$ together are $C_{2-5}$ polymethylene;

either $R_5$ is hydrogen, hydroxy, $C_{1-6}$ alkoxy or $C_{1-7}$ acyloxy and $R_6$ is hydrogen or $R_5$ and $R_6$ together are a bond;

$R_7$ is hydrogen, $C_{1-6}$ alkyl, $C_{1-6}$ alkoxy, hydroxy, halogen, trifluoromethyl, nitro, cyano, $C_{1-12}$ carboxylic acyl, or amino or aminocarbonyl optionally substituted by one or two $C_{1-6}$ alkyl;

X is oxygen or sulphur;

n is 1 or 2; the nitrogen-containing group in the 4-position being trans to the $R_5$ group when $R_5$ is hydroxy, $C_{1-6}$ alkoxy or $C_{1-7}$ acyloxy; or a pharmaceutically acceptable salt or solvate thereof.

2. A compound according to claim 1, wherein one of $R_1$ and $R_2$ is hydrogen and the other is selected from the class of $C_{1-6}$ alkylcarbonyl, $C_{1-6}$ alkoxycarbonyl, nitro and cyano.

3. A compound according to claim 2, wherein $R_2$ is hydrogen and $R_1$ is nitro or cyano.

4. A compound according to claim 1, wherein $R_3$ and $R_4$ are both methyl.

5. A compound according to claim 1, wherein $R_5$ is hydroxy, $C_{1-6}$ alkoxy or $C_{1-7}$ acyloxy and $R_6$ is hydrogen.

6. A compound according to claim 1, wherein n is 2.

7. 6-cyano-3,4-dihydro-2,2-dimethyl-trans-4- (N-tetrahydroisoquinolin-1-one)-2H-benzo[b]-pyran-3-ol.

8. A pharmaceutical composition for the treatment of hypertension comprising an effective amount of a compound according to claim 1 or a pharmaceutically acceptable salt or solvate thereof and a pharmaceutically acceptable carrier.

9. A method of treating hypertension in mammals including man, which comprises administering to the sufferer an anti-hypertensive amount of the compound according to claim 1 or a pharmaceutically acceptable salt thereof.

* * * * *